US00PP07978P

United States Patent [19]

Twomey

[11] Patent Number: Plant 7,978

[45] Date of Patent: Sep. 22, 1992

[54] SHRUB ROSE PLANT NAMED TWOADVANCE

[75] Inventor: Jerry Twomey, Leucadia, Calif.

[73] Assignee: DeVor Nurseries, Inc., Watsonville, Calif.

[21] Appl. No.: 640,861

[22] Filed: Jan. 11, 1991

[51] Int. Cl.[5] ..... A01H 5/00

[52] U.S. Cl. ..... Plt./1

[58] Field of Search ..... Plt. 1, 22, 27

*Primary Examiner*—Howard J. Locker

*Attorney, Agent, or Firm*—Christie, Parker & Hale

[57] ABSTRACT

A new rose plant of the shrub class producing clusters of red flowers.

1 Drawing Sheet

SUMMARY OF THE INVENTION

The present invention relates to a new and distinct variety of rose plant of the shrub rose class which was originated by my crossing as seed parent the variety known as 'Gitte' and as pollen parent an unnamed and unpatented seedling of my creation. The varietal denomination of this new rose is 'Twoadvance' and its commercial name is 'All That Jazz'.

Among the novel characteristics possessed by this new variety which distinguishes it from its parents and all other varieties of which I am aware are its attractive red flowers borne on a shrub size plant particularly suitable for use in gardens. Flowers open well and hold their coloring as blooms age. The new variety is also characterized by its health, vigor and flower production as well as its outstanding resistance to mildew, black spot, rust and botrytis.

Asexual reproduction by budding and rooting of cuttings of the new variety as performed in Glenn County, Calif. and Kern County, Calif., shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

'Twoadvance' is an unusually fine shrub rose of red flower coloration. It is especially well suited for landscape use and growing outdoor in gardens. The variety blooms freely under natural growing conditions. The foliage is dark green, semi leathery and holly-like.

The following is a detailed description of my new variety, with color terminology in accordance with The Royal Horticultural Society Colour Chart (R.H.S.C.C.). The terminology used in color description herein refers to plate numbers in the aforementioned color chart.

Parentage: Seedling.

*Seed parent.*—'Gitte'.

*Pollen parent.*—Unnamed Seedling.

Class: Shrub.

The following information is from observations made of specimens grown outdoors in Watsonville, Calif.

FLOWER

Blooming habit: Continuous, profuse.

A. Bud:

(1) *Size.*—Medium; about 2.5 cm in diameter and 3 to 4.5 cm in length.

(2) *Form.*—Medium, pointed, slow opening.

(3) *Color.*—As sepals divide, bud color is near 45A to 44A.

(4) *Sepals.*—5 in number; longer than bud; foliaceous; tend to curl back as petals unfurl. Color: Inside — near 148C. Outside — near 146A with tinges of near 166A.

(5) *Peduncle.*—Length: 5 cm to 6 cm; small spines. Aspect: Straight. Strength: Erect, slender. Color: Near 144A with near 166A on some sides.

(6) *Calyx.*—Shape: Funnel shaped; does not split; smooth aspect. Size: Medium; 1 cm×1 cm.

B. Bloom:

(1) *Size.*—Large, average size when fully expanded — about 11 to 12 cm; depth about 4.5 to 5 cm.

(2) *Borne.*—Clusters.

(3) *Form.*—Cupped.

(4) *Petalage.*—Number of petals under normal conditions — about 12 to 13; 1 to 2 petaloids.

(5) *Color.*—After sepals fall and petals unfurl, bud coloration is near 45A to 46A. As flower opens, predominant flower color viewing petals' top surface is near 50A to B. Color is general and substantially constant. Petal undersurface displays similar coloration though of slightly lighter hue. Color at point of petal attachment is near 9A.

C. Petals:

(1) *Texture.*—Medium.

(2) *Appearance.*—Satiny to velvety.

(3) *Form.*—Fan shaped to obovate with some indentation or notching at margin and all are slightly lobed at apex.

(4) *Arrangement.*—Regularly arranged, imbricated.

(5) *Fragrance.*—Moderate, fruity.

(6) Lasting *Quality.*—Long lasting on plant and as cut flower; petals drop off cleanly on spent blooms.

Reproductive Organs

A. Stamens:

*Number.*—Approximately 167.

*Arrangement.*—Introrse.

*Anthers.*—Size — 0.3 to 0.4 cm. Color — near 22A.

*Filaments.*—(Threads): Length — 1 to 1.5 cm. Color — near 21B with tinges of near 31A on most threads.

*Pollen.*—Color — near 22A.

B. Pistils: Number — approximately 71.

*Styles.*—Length — 1 to 1.2 cm. Color — near 145D.

*Stigmas.*—Color — near 162A.

C. Characteristics of ovaries: Small, round, flattened, with silvery hairs.

D. Hips:

*Fertile.*—Yes.

*Shape.*—Globular; 2.4 cm wide by 2.1 cm long.

*Color at maturity.*—Near 196A.

Plant

A. Form: Upright shrub type.

B. Growth: Vigorous, upright; free branching; height attained about 119 cm to 130 cm at three years; flowering stems off main canes approximately 66 cm.

C. Foliage: Compound 3, 5 and 7 leaflets.

(1) *Size.*—Leaf size about 17 cm×14 cm.

(2) *Quantity.*—Abundant.

(3) *Color.*—Upper side — dark green, near 147A. Under side — near 146A.

(4) *Shape.*—Oval, pointed.

(5) *Texture.*—Semi-leathery; upper side is glossy, under side is matte.

(6) *Edge.*—Serrate, (denticulate).

(7) *Serration.*—Ordinary.

(8) *Leaf stem.*—Color — medium green.

(9) *Stipules.*—Adnate and tipped with glands.

(10) *Petiolule.*—About ¼ cm.

(11) *Rachis.*—About 8.5 to 10 cm on 3 leaf; 16 to 20 cm on 7 leaf.

(12) *Petioles.*—Length — 1 cm on 3 leaf; 2 to 2.25 cm on 7 leaf.

(13) *Ribs and veins.*—Rib depressed but not veins; both rounded underneath; small prickles underneath.

(14) *Resistance to disease: Very resistant to mildew, rust, black spot and botrytis.*

D. Wood (1) *New Wood.*—Color — purple/red. Bark — smooth.

(2) *Old wood.*—Color — near 146B. Bark — smooth.

E. Thorns:

(1) *Thorns.*—Declining, vary in size. Length — medium, about 1¼ cm Color — near 164C tinged with 181A. Position — irregular.

(2) *Prickles.*—Few to none present.

F. Winter hardiness: Needs protection in severe climates.

I claim:

1. A new and distinct variety of rose plant of the shrub rose class, substantially as shown and described.

* * * * *

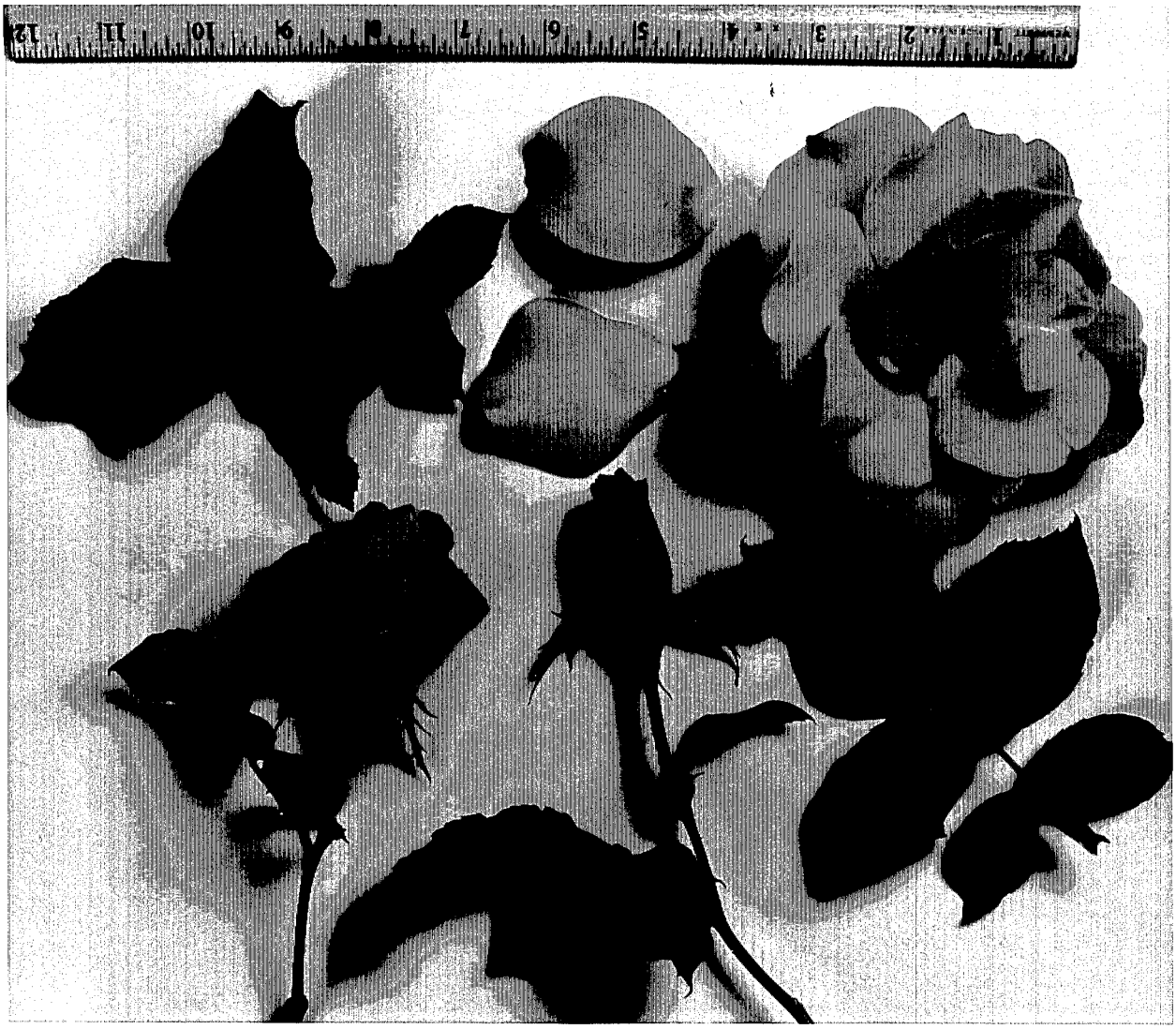

UNITED STATES PATENT AND TRADEMARK OFFICE

CERTIFICATE OF CORRECTION

PATENT NO. : Plant 7978

DATED : September 22, 1992

INVENTOR(S) : Jerry Twomey

It is certified that error appears in the above-identified patent and that said Letters Patent is hereby corrected as shown below:

Column 3, line 17, change "196A" to -- 169A --.

Column 4, line 22, change "164C" to -- 163C --.

Signed and Sealed this

Nineteenth Day of October, 1993

Bruce Lehman

*Attest:*

BRUCE LEHMAN

*Attesting Officer*

*Commissioner of Patents and Trademarks*